United States Patent [19]

Applebaum et al.

[11] Patent Number: 5,615,770
[45] Date of Patent: Apr. 1, 1997

[54] IMPLANT PACKAGE INSERT DELIVERY SYSTEM

[75] Inventors: Edward L. Applebaum, Chicago, Ill.; Brad Beale, Cordova, Tenn.

[73] Assignee: Smith & Nephew, Inc., Memphis, Tenn.

[21] Appl. No.: 513,387

[22] Filed: Aug. 10, 1995

[51] Int. Cl.⁶ .......................... A61B 19/00; A61B 17/06
[52] U.S. Cl. .......................... 206/363; 206/370; 206/438; 206/749; 206/752; 206/759; 206/774
[58] Field of Search .......................... 206/363, 370, 206/438, 439, 738, 747, 749, 752, 754, 755, 759, 760, 774

[56] References Cited

U.S. PATENT DOCUMENTS

| | | |
|---|---|---|
| 2,657,793 | 11/1953 | Goldshine ............... 206/755 |
| 3,013,656 | 12/1961 | Murphy . |
| 4,522,209 | 6/1985 | Patrick et al. . |
| 4,671,410 | 6/1987 | Hansson et al. ............ 206/438 |
| 4,697,703 | 10/1987 | Will ............................ 206/438 |
| 4,750,619 | 6/1988 | Cohen et al. ............... 206/438 |
| 5,148,920 | 9/1992 | Walker ..................... 206/438 X |
| 5,176,258 | 1/1993 | Antal . |
| 5,193,679 | 3/1993 | White ......................... 206/363 |
| 5,236,088 | 8/1993 | Dhority et al. . |
| 5,346,075 | 9/1994 | Nichols et al. . |
| 5,405,005 | 4/1995 | White ......................... 206/363 |
| 5,494,162 | 2/1996 | Treace et al. ............... 206/438 |
| 5,497,875 | 3/1996 | Kuo ............................ 206/751 |

FOREIGN PATENT DOCUMENTS

WO91/11374  8/1991  WIPO ..................... 206/439

*Primary Examiner*—Bryon P. Gehman
*Attorney, Agent, or Firm*—Pravel, Hewitt, Kimball & Krieger

[57] ABSTRACT

A sterilizable medical implant package insert that provides enhanced protection of the implant during shipment and easier access of the implant at its destination. The sterile implant package insert is placed within standard sterile implant packages and provides for the automatic presentation of the implant from the insert when the sterile package top is opened. The insert also provides increased protection of the implants during shipping and operating room manipulation by securely holding the implant, thus preventing damage from collisions between the implant and the container walls and by providing double wall containment.

13 Claims, 4 Drawing Sheets

5,615,770

IMPLANT PACKAGE INSERT DELIVERY SYSTEM

BACKGROUND OF THE INVENTION

1. Field of the Invention

The present invention relates to sterilizable medical implant package inserts that provide enhanced protection of the implant during shipment and easier access of the implant at their destination.

2. Description of the Related Art

Due to the diminutive size and fragile nature of many medical implants, such as otologic implants and ventilation tubes, sterilization/shipping containers must provide protection of the implant, be constructed of materials that retain sterile properties and offer ease of handling to the physician and operating nurses.

Typical existing containers include a depression that is larger than the implant itself. The implant is simply placed in the depression. While such containers may satisfy sterility requirements, they, by nature of design, allow the implants to freely shift positions while in the container. This freedom of movement of the implant within the container tends to damage the implant during shipment. Even if the implant has survived the shipment and arrived at the operating room undamaged, an abrupt opening of the container lid will tend to eject and damage the implant. In addition, the fragile implants are frequently damaged during attempts at their removal from the container, which is often performed by grasping the unsecured implants with forceps while stabilizing the implants by forcing them against the wall of the container.

U.S. Pat. No. 5,176,258 to Antal describes a package which includes a peripheral flange around a blister defining an open cavity for receiving a product and a compressible insert for securing the product against movement in the cavity. The Antal patent defines the blister type package with specific reference to sealed packages, and more specifically to an improved method for sealing. Although reference to medical parts is mentioned, the general theme of the Antal disclosure refers to the process of sealing the package and providing a hermetical seal of that package. In addition, Antal teaches a package and associated package opening procedure whereby the medical device is allowed to drop freely from the package onto a sterile field. Such a dropping technique is not desirable for fragile medical implants.

U.S. Pat. No. 5,148,920 to Walker describes a package including a receptacle containing an opening and defining a space for the product and an insert defining an aperture for the product. When the product is in the insert and the insert within the receptacle, a portion of the insert is between the product and cap over the opening, thereby providing a positive restraint against movement of the product. The package configuration of this invention is particularly aimed at medical implants and instruments. The general theme of the Walker disclosure is to provide a modular system by which different inserts can be provided for the same container to secure different sized products and protect them from abrasion and shock while providing access to the product. The Walker package, however, still requires that the operating room personnel lift the insert out of the container in order to free the medical implant. Further, as the insert contacts the implant, damage to fragile inserts could readily result when the insert contacts the implant. In addition, numerous steps are required to access the implant, increasing the likelihood of damage. Finally, Walker requires that the implant and packaging materials be sterilized prior to packaging, thereby increasing handling difficulties during manufacture. The implant is not automatically presented when the container is opened.

There still exists a need for a medical implant packaging system that is sterilizable, protects and secures fragile implants, automatically presents the implants to operating room personnel in an easily accessible manner as the container is opened, and requires a minimum of handling of either the package or implant during manufacture and in the operating room.

SUMMARY OF THE INVENTION

A sterilizable medical implant package insert according to the present invention provides enhanced protection of the implant during shipment and easier access of the implant at the destination. The sterile implant package insert, which is placed within standard sterile implant packages, provides for the automatic presentation of the implant from the insert once the sterile package top is opened. The insert also provides increased protection of the implants during shipping and operating room manipulation by securely holding the implant, thus preventing damage from collisions between the implant and the container walls, and by providing double wall containment.

The implant package insert is comprised of a base and a lid which is moveable between an open position and a closed position. The shape of the lid and base are such that an at least partially enclosed chamber area is formed when the lid is closed. The lid is attached to the base by a means which moves the lid to the open position and holds it there in the absence of externally applied force. The attaching means allows the lid to move to the closed position upon the application of force to the lid. The implant package insert may have a vent, through which sterilization gases can pass into the chamber area.

The implant package insert further comprises means for securely holding at least one implant and for presenting the implant for easily accessible removal from the holding means when the lid is in the open position. The implant is protected during shipment by being held in the chamber. The shape of the insert allows the insert base to be securely held within the depression of a standard sterilizable implant package while the depression side walls do not obstruct the insert lid's movement.

BRIEF DESCRIPTION OF DRAWINGS

The invention will be become more fully understood, and the advantages will become apparent, in the following detailed description of a preferred embodiment of the invention illustrated in the accompanying drawings.

DETAILED DESCRIPTION OF THE PREFERRED EMBODIMENT

Figure 1:
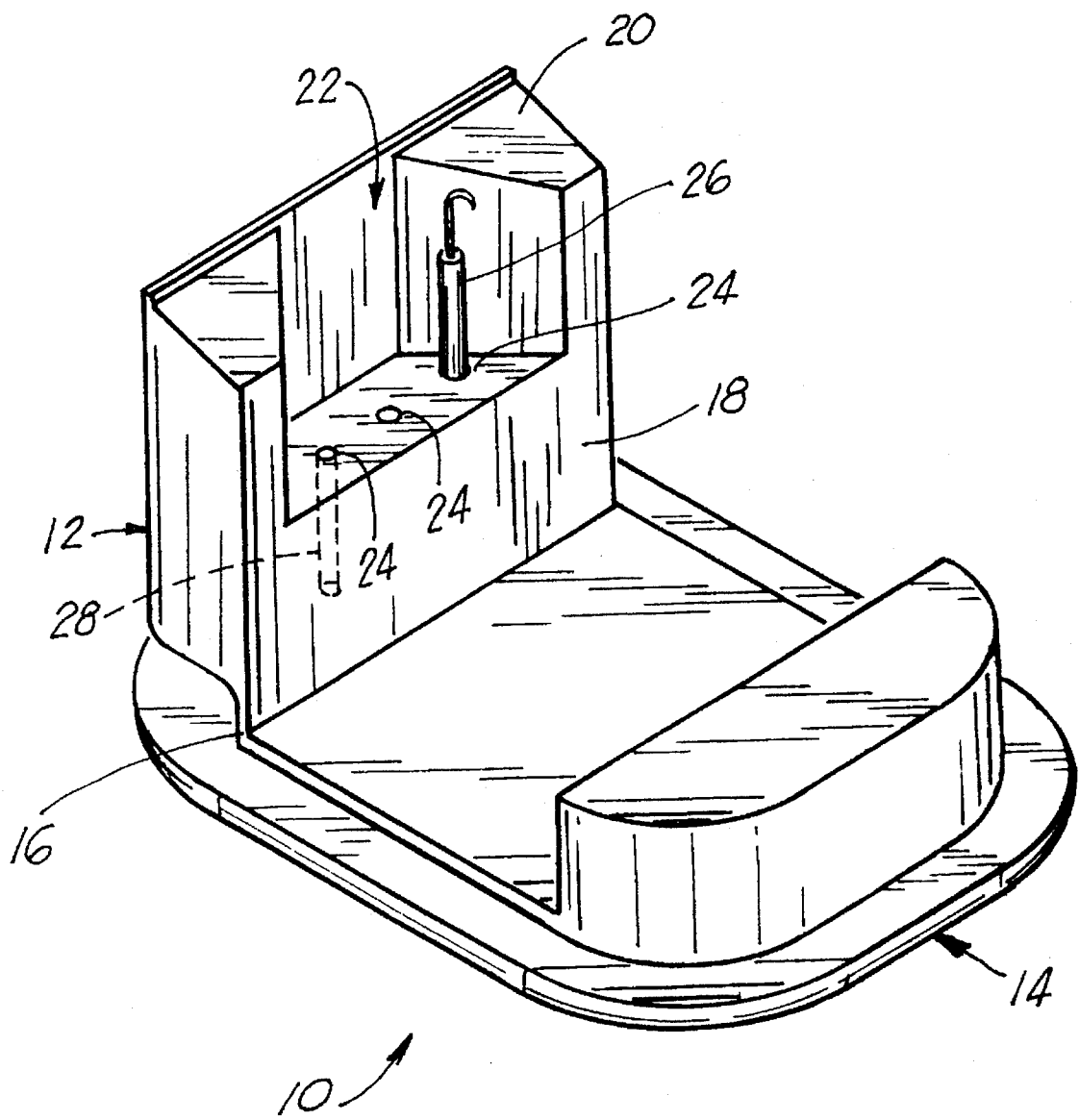
FIG. 1 is an isometric view of an implant package insert according to the present invention, in the open position and holding an implant.

Referring to FIG. 1, a preferred implant package insert 10 includes a lid 12, a base 14, and a hinge 16. Preferably the lid 12, base 14 and hinge 16 are manufactured as a single component by injection molding of appropriate plastic material, though other materials and manufacturing techniques can be used.

The lid 12 includes a lower surface 18 and a front surface 20. The lid 12 is connected to the base 14 by an attaching means, preferably a hinge 16. Preferably the hinge 16 is manufactured of the same material as the remainder of the insert and is constructed as a relatively thin section of that material. Preferably the lid 12 is molded in a slightly or fully open position so that the natural resiliency of the hinge 16 material can be utilized. The hinge 16 automatically moves the lid 12 to the natural open position, as illustrated in FIG. 1, when no external force is applied. The lid 12 moves to a closed position (FIG. 2) when an external force is applied to the top of the lid 12.

The lower surface 18 of the lid 12 includes a recessed area 22, in which there are cavities 24 that serve as receptacles for implants, for example the middle ear implant 26 of FIG. 1. Preferably the cavities 24 are different sizes to receive different sizes and shapes of implants. The recessed area 22 is sufficient to allow clearance between the base 14 and the lid 12 when the implant is installed and the lid 12 is closed.

Figure 2:
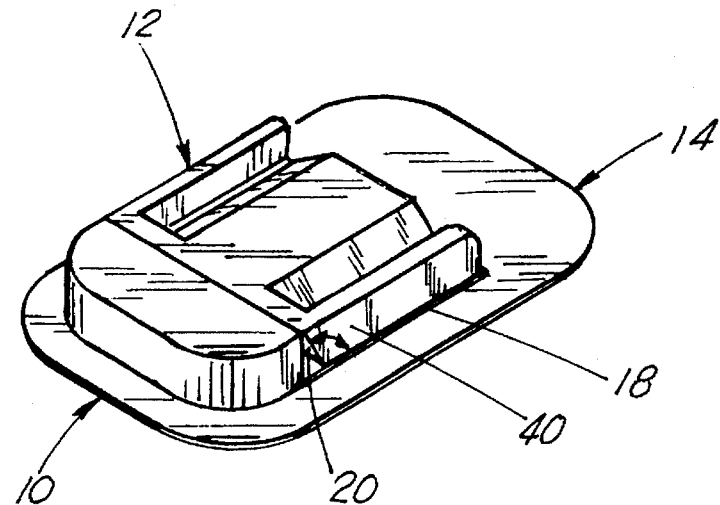
FIG. 2 is an isometric view of the implant package insert of FIG. 1 in the closed position.
Figure 3:
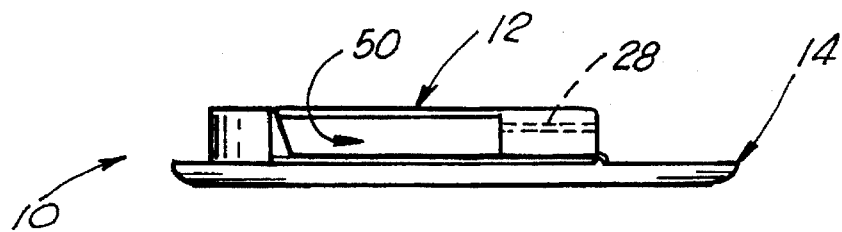
FIG. 3 is a cross-sectional side view of the implant package insert of FIG. 1 in the closed position.

FIGS. 2 and 3 illustrate the insert 10 with the lid 12 in the closed position. The lid front surface 20 makes an angle 40 greater than 90° with the lid lower surface 18, for ease of closure and for ventilation under the lid 12 when closed. The preferred angle 40 is 112°. When the lid 12 is in the closed position, the lid recessed area 22 and the base 14 form a chamber 50, as illustrated in FIG. 3. In the bottom of the cavities 24 are vents 28, also as illustrated in FIG. 1, in order to allow sterilization gases, for example ethylene oxide, to have an access to the chamber 50. In a preferred embodiment, the vents 28 are formed by extending a cavity 24 through the lid 12 to an outer surface of the lid 12.

Figure 4:
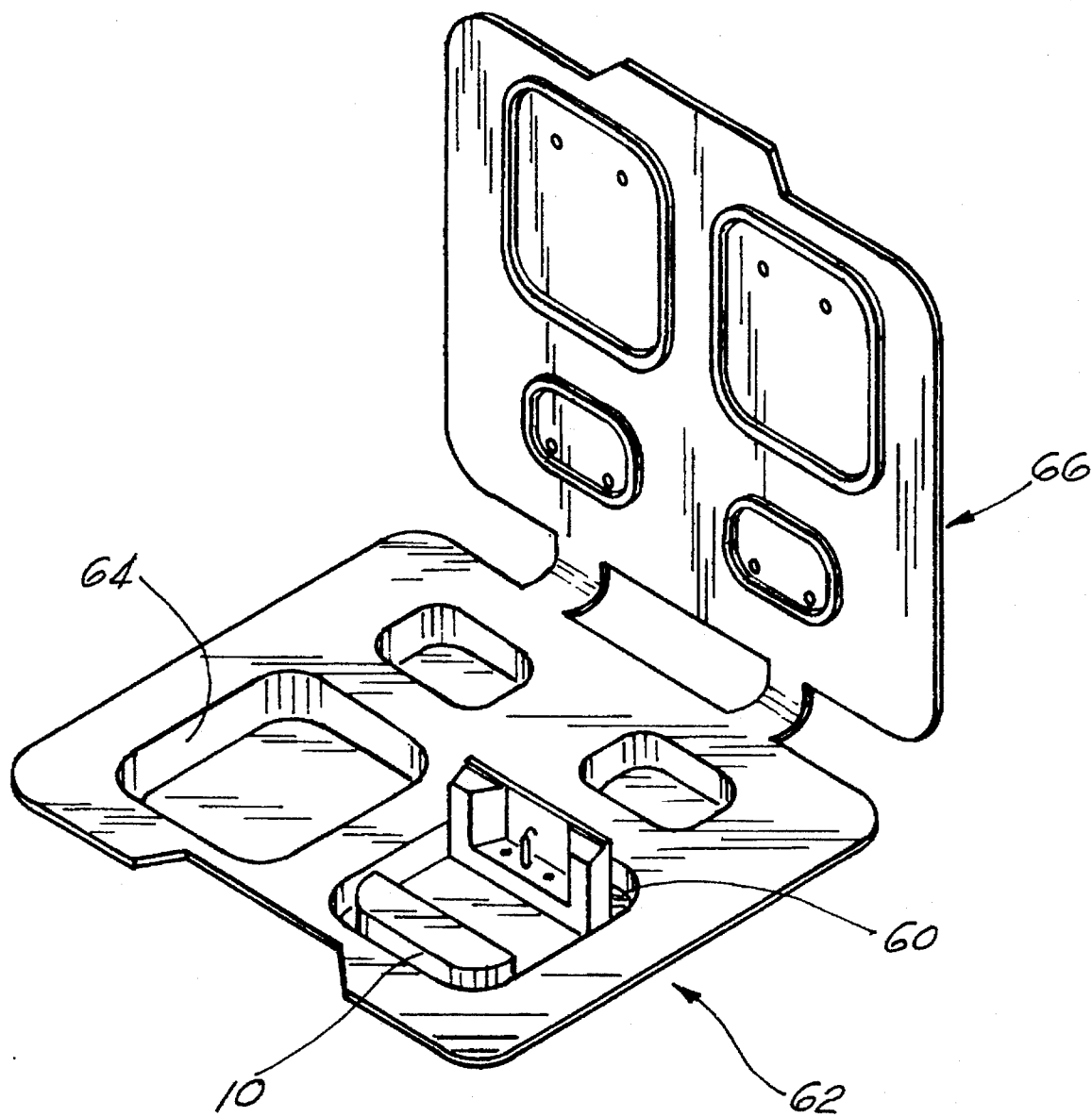
FIG. 4 is an isometric view of the implant package insert of FIG. 1 seated in a depression of a standard implant package.
Figure 5:
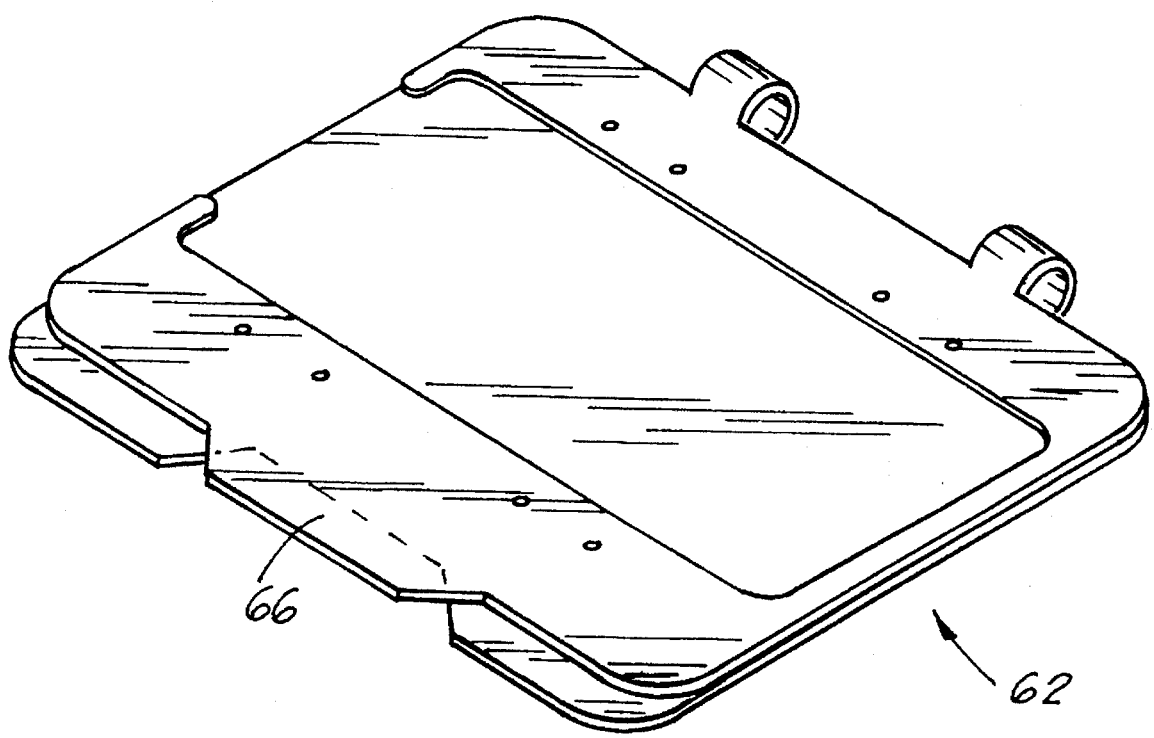
FIG. 5 is an isometric view of the implant package of FIG. 4 in the closed position.

Referring to FIGS. 4 and 5, the preferred embodiment of the implant package insert 10 is designed to be placed in a package depression 60 of a sterile implant package 62. In the preferred embodiment, the insert 10 is held securely in the package depression 60 by a snug fit between the insert base 14 and the walls 64 of the depression 60. In the preferred embodiment, the shape and size of the lid 12 is such that the lid's movement is not obstructed by the depression walls 64. While implant package 62 is in the closed position, as in FIG. 5, the insert 10 remains in the closed position due to the force exerted on the insert lid 12 by the package top 66. When the implant package top 66 is in the open position, as in FIG. 4, the insert lid 12 automatically elevates, by natural action of the hinge 16, into an open position and the implant 26, held partially in the cavity 24 of the lid 12, is presented for easy access by medical personnel.

In the preferred embodiment, once the implant package insert 10 is placed into the package depression 60, the package insert 10 need not be removed from the depression. The implant package insert 10 remains stationary in the depression 60 as the lid 12 opens to present the implant 26. The insert 10 and implant package 62 of the preferred embodiment are preferably disposable.

While the depression 60 is shown in FIG. 4 as being entirely in the package bottom, with the package top 66 being generally planar, it is understood that the depression 60 could be formed partially in the package bottom and partially in the package top 66 by reducing the depth in the package bottom and providing a depression or chamber area in the package top 66, so that the depression 60 effective height is then the sum of the two individual depressions.

The insert 1 may be made of any suitable materials. Suitable materials of construction include those that are compatible with the implant to be stored and the sterilization process. Suitable materials include, but are not limited to, polymeric materials, such as polypropylene, polyethylene and polyvinyl chloride.

A preferred implant package insert 10 for use with stapes prostheses (middle ear inserts), as illustrated in FIG. 1, was constructed by injection molding of polypropylene. The width of the base 14 of the insert 10 was approximately 0.75", the length approximately 1", and the height in the closed position approximately 0.25". Of course, the insert 10 can be sized differently to accommodate differently sized implants and differently sized implant packages.

The invention has been described with reference to its preferred embodiments. From this description, it should be understood that various changes, alterations and substitutions can be made by a person of ordinary skill in the art without departing from the scope and spirit of the invention as described above and claimed hereafter.

What is claimed is:

1. A sterilizable medical implant package insert for placement in a depression of a sterilizable implant package, the insert comprising:

a base sized to securely fit within the package depression;

a lid sized to fit within the package depression, said lid including holding means for removably and securely holding an implant, said lid and said base having a combined height less than the effective height of the package depression; and attaching means for pivotally attaching said lid to said base, said attaching means adapted to automatically elevate said lid and hold said lid in an open position in the absence of external forces and to allow said lid to pivot into a closed position by an application of external force to said lid, said lid being pivotable between said open and said closed position, said lid and said base adapted to define an at least partially enclosed chamber therebetween when said lid is in said closed position, said holding means securely holding an implant at least partially within said chamber when said lid is in said closed position and presenting an implant for removal in an accessible manner when said lid is in said open position.

2. The implant package insert of claim 1 wherein said holding means is a cavity in said lid.

3. The implant package insert of claim 2, wherein said lid includes vents extending from said cavity for allowing communication of sterilization gases into said chamber.

4. The implant package insert of claim 2, wherein said lid includes an opening on a side other than that containing said cavity for allowing communication of sterilization gases into said chamber.

5. The implant package insert of claim 2, wherein said cavity is sized to securely hold an otologic implant.

6. The implant package insert of claim 1, wherein said lid further includes a recess, said recess at least partially defining said chamber when said lid is in said closed position.

7. The implant package insert of claim 1, wherein the insert is a unitary piece.

8. The implant package insert of claim 7, wherein the insert is produced by injection molding.

9. The implant package insert of claim 7, wherein the insert is fabricated of a polymeric material.

10. The implant package insert of claim 9, wherein said polymeric material is polypropylene.

11. The implant package insert of claim 1, wherein said attaching means is a hinge.

12. The implant package insert of claim 11, wherein both the base and lid are fabricated of a single material and said hinge is a thinned section of said single material.

13. The implant package insert of claim 1 wherein the lid and attaching means are sized and adapted such that when the insert base is securely fit within the package depression, the lid is in the closed position when the implant package is closed and the lid automatically elevates to the open position when the implant package is opened.

* * * * *